United States Patent [19]

Ince et al.

[11] Patent Number: 4,883,804
[45] Date of Patent: Nov. 28, 1989

[54] AROMATIC COMPOUNDS

[75] Inventors: Francis Ince, Loughborough; Brian Springthorpe, Shepshed; John Dixon, Melton Mowbray, all of England

[73] Assignee: Fisons plc, Ipswich, England

[21] Appl. No.: 932,473

[22] Filed: Nov. 19, 1986

[30] Foreign Application Priority Data

Nov. 20, 1985 [GB] United Kingdom ............... 85/28605
Jul. 10, 1986 [GB] United Kingdom ............... 86/16792
Jul. 10, 1986 [GB] United Kingdom ............... 86/16793
Jul. 10, 1986 [GB] United Kingdom ............... 86/16794

[51] Int. Cl.$^4$ .................... C07C 87/28; C07D 239/02; A01N 37/30; A61K 31/205
[52] U.S. Cl. .................... 514/357; 514/603; 514/608; 514/649; 514/651; 514/654; 514/821; 514/822; 514/824; 546/329; 546/334; 564/341; 564/354; 564/363; 564/367
[58] Field of Search ............ 564/341, 367, 354, 363; 514/357, 603, 608, 649, 651, 654, 821, 822, 824; 546/329, 334

[56] References Cited

U.S. PATENT DOCUMENTS

| 3,789,072 | 1/1974 | Bernstein .......................... 260/557 B |
| 4,010,280 | 3/1977 | Marayamo et al. ................. 424/316 |
| 4,720,586 | 1/1988 | Dixon et al. ........................ 564/341 |

FOREIGN PATENT DOCUMENTS 1191846  8/1985  Canada ............................... 564/367

Primary Examiner—Richard L. Raymond
Assistant Examiner—Raymond Covington
Attorney, Agent, or Firm—Marshall Gerstein, Murray & Bicknell O'Toole

[57] ABSTRACT

There are described compounds of formula I,

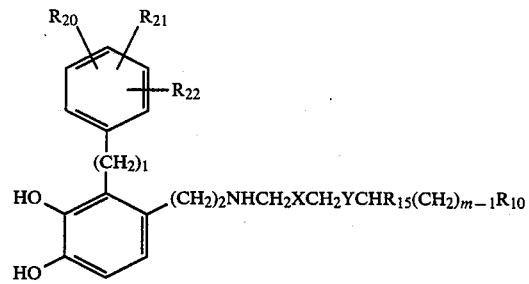

in which X represents a C2 to 8 alkylene chain optionally interrupted by a double bond or by $S(O)_n$, wherein n is 0, 1 or 2;

Y represents O or NH,
l and m each independently represent 2, 3 or 4,
$R_{10}$ represents phenyl substituted by one or more substituents $R_{23}$, which may be the same or different; or $R_{10}$ represents pyridyl, a saturated carbocyclic group, alkyl C 1 to 6 or hydrogen,
$R_{15}$ represents hydrogen or together with $R_{23}$ forms a $(CH_2)_p$ chain, wherein p represents 0, 1 or 2;
$R_{20}$, $R_{21}$, $R_{22}$ and $R_{23}$, which may be the same or different, independently represent hydrogen, alkyl C 1 to 6, $NHR_{25}$, SH, $NO_2$, halogen, $CF_3$, $SO_2R_{30}$, $CH_2OH$ or OH, wherein $R_{25}$ represents hydrogen, alkyl C 1 to 6, alkanoyl C 1 to 6 or $SO_2$ alkyl C 1 to 6, and $R_{30}$ represents alkyl C 1 to 6 or $NH_2$,
provided that when X represents an uninterrupted C4 alkylene chain, Y represents NH, m represents 2, 1 represents 2, $R_{10}$ represents phenyl, $R_{15}$ represents hydrogen, and $R_{21}$, $R_{22}$ and $R_{23}$ represent hydrogen, then $R_{20}$ does not represent hydrogen or 4-OH,
and pharmaceutically acceptable salts and solvates thereof.

There are also described processes for the preparation of the compounds of formula I and pharmaceutical compositions containing them. The compounds of the invention may be used in the treatment or prophylaxis of renal failure or cardiovascular disorders.

10 Claims, No Drawings

AROMATIC COMPOUNDS

This invention relates to novel compounds, compositions thereof and processes for their preparation.

According to the invention there are provided compounds of formula I,

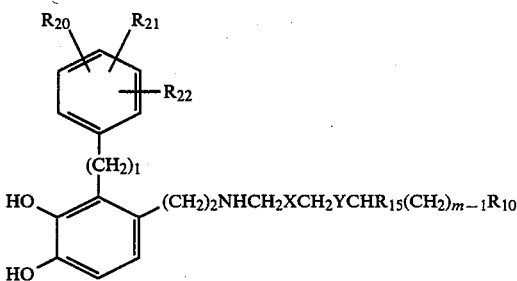

in which X represents a C2 to 8 alkylene chain optionally interrupted by a double bond or by $S(O)_n$, wherein n is 0, 1 or 2;

Y represents O or NH, l and m each independently represent 2, 3 or 4, $R_{10}$ represents phenyl substituted by one or more substituents $R_{23}$, which may be the same or different; or $R_{20}$ represents pyridyl, a saturated carbocyclic group, alkyl C 1 to 6 or hydrogen, $R_{15}$ represents hydrogen or together with $R_{23}$ forms a $(CH_2)_p$ chain, wherein p represents 0, 1 or 2;

$R_{20}$, $R_{21}$, $R_{22}$ and $R_{23}$, which may be the same or different, independently represent hydrogen, alkyl C 1 to 6, $NHR_{25}$, SH, $NO_2$, halogen, $CF_3$, $SO_2R_{30}$, $CH_2OH$ or OH, wherein $R_{25}$ represents hydrogen, alkyl C 1 to 6, alkanoyl C 1 to 6 or $SO_2$ alkyl C 1 to 6, and $R_{30}$ represents alkyl C 1 to 6 or $NH_2$, provided that when X represents an uninterrupted C4 alkylene chain, Y represents NH, m represents 2, l represents 2, $R_{10}$ represents phenyl, $R_{15}$ represents hydrogen, and $R_{21}$, $R_{22}$ and $R_{23}$ represent hydrogen, then $R_{20}$ does not represent hydrogen or 4-OH, and pharmaceutically acceptable salts and solvates thereof.

According to the invention, there is also provided a process for the preparation of compounds of formula I or pharmaceutically acceptable salts or solvates thereof, which comprises removing a protecting group from a compound of formula II,

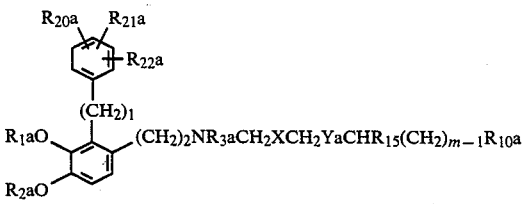

in which Ya represents O or $NR_{4a}$,

X, $R_{15}$, m and l are as identified above, $R_{1a}$, $R_{2a}$, $R_{3a}$ and $R_{4a}$, which may be the same or different, represent hydrogen or a protecting group, $R_{10a}$ has the same significance as $R_{10}$ above, save that when $R_{10a}$ represents phenyl, it may be substituted by one or more substituents $R_{23a}$, $R_{20a}$, $R_{21a}$, $R_{22a}$ and $R_{23a}$ respectively have the same significances as $R_{20}$, $R_{21}$, $R_{22}$ and $R_{23}$ above, save that in addition they may represent $NR_{25}R_{26a}$, $SR_{27a}$, $CH_2OR_{28a}$ or $OR_{29a}$, wherein $R_{26a}$, $R_{27a}$, $R_{28a}$ and $R_{29a}$, which may be the same or different, each represents a protecting group and $R_{25}$ is as defined above, provided that the compound of formula II bears at least one protecting group and where desired or necessary converting the resulting compound of formula I to a pharmaceutically acceptable salt or solvate thereof, or vice versa.

Protecting groups that $R_{1a}$, $R_{2a}$, $R_{3a}$, $R_{4a}$, $R_{26a}$, $R_{27a}$, $R_{28a}$ and $R_{29a}$ may represent include, for example, alkyl C 1 to 6, especially methyl; phenylalkyl C7 to 12, especially benzyl; alkanoyl C2 to 6, such as acetyl and haloalkanoyl C2 to 6, especially trifluoroacetyl. In addition, the protecting group may protect two functional groups, for example $R_2$ and $R_3$ may together represent

Other protecting groups are well known and include those described in Protective Groups in Organic Chemistry, ed: J W F McOmie, Plenum Press (1973), and Protective Groups in Organic Synthesis, T W Greene, Wiley-Interscience (1981).

Removal of the protecting group depends on the nature of the protecting group; conventional techniques may generally be employed, including acidic or basic cleavage or hydrogenolysis. For example, protecting alkyl or phenylalkyl groups may be removed by cleavage using a protic acid, e.g. hydrochloric acid or a hydrobromic acid at a temperature of from about 0° to 150° C., or a Lewis acid, e.g. by reacting with boron trihalide in a halocarbon solvent. 1-Phenylalkyl groups, e.g. benzyl, may be removed by catalytic hydrogenation using a suitable catalyst, e.g. palladium, in a suitable solvent, e.g. methanol or acetic acid. Further methods for the removal of protecting groups are described in both McOmie and Greene, loc. cit. Both McOmie and Greene also describe numerous methods for the application of protecting groups.

Compounds of formula II in which X is interrupted by SO or $SO_2$ may be made from the corresponding compounds of formula II in which X is interrupted by S, by protection of the nitrogen atom(s), e.g. using trifluoracetic anhydride, oxidation, e.g. using m-chlorperbenzoic acid, and deprotection of the nitrogen atom(s).

Compounds of formula II in which X is interrupted by S or by a double bond may be made by reducing a corresponding compound of formula III,

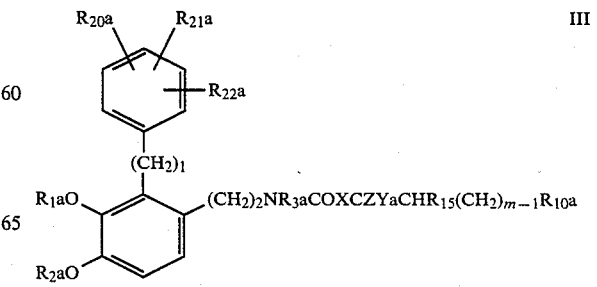

in which Z represents $H_2$ when Ya represents O, and O when Ya represents $NR_{4a}$, and $R_{1a}$, $R_{2a}$, $R_{3a}$, $R_{4a}$, $R_{15}$, $R_{10a}$, $R_{20a}$, $R_{21a}$, $R_{22a}$, X, Ya, l and m are as defined above.

The reducing agent may be electrophilic, for example diborane, or nucleophilic, for example, a complex metal hydride such as lithium aluminium hydride or sodium (2-methoxyethoxy) aluminium hydride. The reaction may be carried out in a suitable solvent inert to the reaction conditions. Aprotic solvents are preferred, for example tetrahydrofuran, diethyl ether or 1,2-dimethoxyethane. The reaction may be carried out at a temperature of, for example, from 0° to 100° C.

Compounds of formula III in which Ya represents $NR_{4a}$ may be prepared by condensing a compound of formula IV,

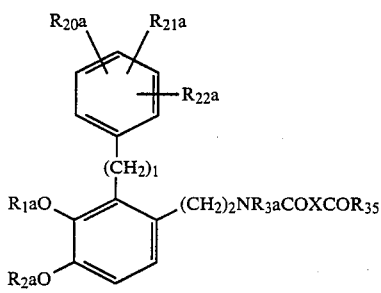

IV in which $R_{35}$ represents OH, and $R_{1a}$, $R_{2a}$, $R_{3a}$, $R_{20a}$, $R_{21a}$, $R_{22a}$, X and l are as defined above, with a compound of formula V,

$HYaCHR_{15}(CH_2)_{m-1}R_{10a}$  V in which Ya, $R_{10a}$, $R_{15}$ and m are as defined above.

The condensation may be carried out under conditions similar to those used for the synthesis of peptide bonds in protein chemistry, e.g. by carrying out the reaction in the presence of N,N'-carbonyldiimidazole in a polar aprotic solvent or using a hindered base, e.g. triethylamine and an alkyl chloroformate. The condensation may also be carried out by reacting the acid chloride of the compound of formula IV with the compound of formula V.

Compounds of formula IV in which $R_{35}$ represents OH may be prepared from the corresponding compound of formula IV in which $R_{35}$ represents alkoxy by hydrolysis, e.g. using sodium hydroxide in water.

Compounds of formula IV in which $R_{35}$ represents alkoxy may be prepared by condensing a compound of formula VI,

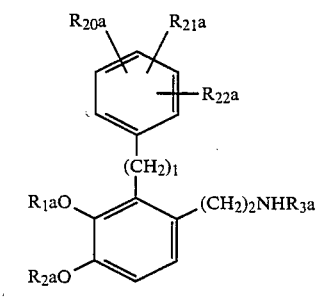

VI in which $R_{1a}$, $R_{2a}$, $R_{3a}$, $R_{20a}$, $R_{21a}$, $R_{22a}$ and l are as defined above, with a compound of formula VII,

$HO_2CXCOalkoxy$  VII in which X is as defined above.

The condensation may be carried out under conditions analogous to those described above for the preparation of compounds of formula III.

The compounds of formula III may also be prepared by condensing a compound of formula VI with a compound of formula VIII,

$HO_2CXC(Z)YaCHR_{15}(CH_2)_{m-1}R_{10a}$  VIII in which X, Ya, Z, $R_{10a}$, $R_{15}$ and m are as defined above.

The condensation may be carried out under conditions analogous to those described above.

The compounds of formulae V, VI, VII and VIII are either known or may be made by conventional techniques known per se.

Acid addition salts of compounds of formula I may be converted to the corresponding free-base by the action of a stronger base. The acid addition salts of the compound of formula I may be prepared by reaction of the free base with an appropriate acid.

Pharmaceutically acceptable acid addition salts of the compounds of formula I include salts of mineral acids, for example, hydrohalic acids, e.g. hydrochloric or hydrobromic acid; or organic acids, e.g. formic, acetic or lactic acids. The acid may be polybasic, for example sulphuric, fumaric or citric acid.

Solvates of the compounds of formula I and their salts include solvates in particular, hydrates of the salts of formula I, e.g. hemihydrates, monohydrates and sesquihydrates.

We prefer compounds of formula I in which $R_{10}$ represents phenyl substituted by one or more substituents $R_{23}$. We prefer $R_{10}$, when it represents phenyl, to be substituted by hydrogen or by one, two or three substituents other than hydrogen. Preferred groups that $R_{23}$ may represent include hydrogen, halogen, e.g. fluorine or chlorine; hydroxy, $NH_2$, $NHSO_2$alkyl C 1 to 6, $NO_2$ or alkyl C 1 to 6, e.g. methyl or ethyl. We particularly prefer compounds in which $R_{10}$ is substituted by one or more hydroxy groups, e.g. 4-OH. Groups that $R_{10}$ may particularly represent include halodihydroxyphenyl, e.g. fluoro-dihydroxyphenyl; halohydroxyphenyl, e.g. fluoro-hydroxyphenyl; hydroxyphenyl, e.g. 3- or 4-hydroxyphenyl; dihydroxyphenyl, e.g. 3,4-dihydroxyphenyl or 2,3-dihydroxyphenyl.

When $R_{10}$ represents a saturated carbocyclic group, preferred carbocyclic groups include those with 5 to 7 inclusive ring atoms, especially six, i.e. cyclohexyl.

When $R_{15}$ together with $R_{23}$ forms a chain, the group $CHR_{15}(CH_2)_{m-1}R_{10}$ may represent 2-(1,2,3,4-tetrahydronaphthalenyl), 1-(benzcyclobutenyl) or especially 2-indanyl.

Alkyl groups that $R_{10}$ may represent include methyl, ethyl, propyl or butyl.

We prefer compounds of formula I in which $R_{20}$, $R_{21}$ and $R_{22}$ independently represent hydrogen, hydroxy, alkyl C 1 to 6, e.g. methyl or ethyl; halogen, e.g. chlorine or fluorine, or trifluoromethyl Compounds of formula I that may particularly be mentioned include those in which at least one of $R_{20}$, $R_{21}$ and $R_{22}$ represents hydroxy. We particularly prefer compounds in which one of $R_{20}$, $R_{21}$ and $R_{22}$ represents 3-hydroxy. Compounds that may also be specifically mentioned include those in which two of $R_{20}$, $R_{21}$ and $R_{22}$ represent hydroxy.

We prefer compounds of formula I in which X represents a C3 to C7, more preferably a C4 to C6 inclusive alkylene chain.

We prefer compounds of formula I in which Y represents NH.

We prefer compounds of formula I in which l represents 2 or 3, especially 2.

We prefer compounds of formula I in which m represents 2 or 3, especially 2.

The compounds of formula I, and pharmaceutically acceptable acid addition salts thereof, are useful because they possess pharmacological activity in animals. Thus the compounds act on peripheral and/or central dopamine receptors. As such, they lower blood pressure and increase blood flow to certain vascular beds, e.g. renal beds. Activity of the compounds has been investigated in the following assay systems:

(a) canine renal blood flow, McNay and Goldberg, J. Pharmac, Exp. Ther., 151, 23–31, 1966.

(b) rabbit isolated ear artery, McCullogh, Rand and Story, Br. J. Pharmac, 49, 141–142, 1973.

(c) guinea pig tracheal chains, Akcasu, Arch. Int. Pharmacodyn. Ther., 122, 201–207, 1959.

(d) guinea pig atria: O'Donnell and Wanstall, J. Pharm. Pharmacol., 31, 686–690, 1979.

The compounds of the invention are indicated for use in the treatment of congestive heart failure, renal failure, angina pectoris, ischaemic heart disease and hypertension. The compounds of the invention are also indicated for use in the treatment of shock and other low cardiac output states of varying aetiology, acute cerebrovascular disease and improvement of the blood supply to and healing of intestinal anastomoses and stomata.

The dosage administered will naturally depend on the compound employed, the mode of administration and the desired effect. However, in general, satisfactory results are obtained when the compound is administered at a dosage of from 0.05 $\mu$g to 50mg per kilogram of body weight per day. For man, the indicated total daily dosage is in the range 2.5 $\mu$g to 3.5g, which may be administered in divided doses of, for example 1 $\mu$g to 750mg.

The compounds of formula I, and pharmaceutically acceptable derivatives thereof, have the advantage that they are more efficacious or produce less undesirable side effects in certain pharmacological models than compounds of similar structure to the compound of formula I.

The compound of the invention may be administered by a wide variety of routes and may act systemically or locally. Thus the compound may be administered by oral or nasal inhalation to the lung, to the buccal cavity, oesophageally, rectally, topically to the skin or to other available surfaces of the body, e.g. the eye, by injection, e.g. intravenously, intramuscularly, intraperitoneally, by instillation or by surgical implant.

According to our invention we also provide a pharmaceutical composition comprising preferably less than 80%, and more preferably less than 50%, by weight of a compound of formula I, or a pharmaceutically acceptable derivative thereof, in admixture with a pharmaceutically acceptable adjuvant, diluent or carrier. Examples of suitable adjuvants, diluents or carriers are: for tablets, capsules and dragees; microcrystalline cellulose, calcium phosphate, diatomaceous earth, a sugar such as lactose, dextrose or mannitol, talc, stearic acid, starch, sodium bicarbonate and/or gelatin;

for suppositories; natural or hardened oil or waxes; and for inhalation compositions, coarse lactose.

When the compound is to be used in aqueous solution it may be necessary to incorporate a chelating or sequestering agent, e.g. sodium edetate, an antioxidant, e.g. sodium metabisulphite or buffering agents, e.g. sodium hydrogen phosphate and sodium phosphate. Aqueous solutions typically contain up to about 10% w/w of the new compound and may be used for intravenous injections.

According to the invention, we further provide a method of treatment of acute renal failure in an animal, either human or non-human, which method comprises administering to the animal an effective amount of the compound of the invention or a pharmaceutically acceptable acid addition salt thereof.

The invention is illustrated, but in no way limited by the following Examples in which temperatures are in degrees Centigrade.

A. Preparation of Intermediates

1. Preparation of 4,4-dimethyloxazoles (a) 2-[3,4-Dimethoxy-2-(2-[3-methoxyphenyl]ethyl)-phenyl]-4,5-dihydro-4,4-dimethyloxazole A solution of 2-(3-methoxyphenyl)ethylbromide (12.2 g) in dry tetrahydrofuran (20 ml) was added dropwise to a suspension of magnesium (1.46 g) in dry tetrahydrofuran (20 ml), under an atmosphere of nitrogen, at a rate sufficient to maintain a state of reflux. After 1 hour the cooled solution was added to a stirred solution of 4,5-dihydro-4,4-dimethyl-2-(2,3,4-trimethoxyphenyl)oxazole (7.95 g) in dry tetrahydrofuran (50 ml) under an atmosphere of nitrogen. The mixture was stirred at 20° for 16 hours. Water (400 ml) was added and the aqueous phase thoroughly extracted with ethyl acetate (2×250 ml). The organic phase was dried over magnesium sulphate, filtered and the solvent removed in vacuo to yield a yellow oil which was purified by flash column chromatography on silica gel, using 10% ethyl acetate/90% petroleum ether as eluent, and by Kugelruhr distillation (air bath temperature 200°/1 mm Hg) 9.7 g of the title compound were obtained. MS m/e 369.

The following oxazoles were prepared by the method of Intermediate 1 (a):

(b) 2-[3,4-Dimethoxy-2-[2-[3-methylphenyl]ethyl]-phenyl]-4,5-dihydro-4,4-dimethyloxazole, m/e 353

(c) 2-[3,4-Dimethoxy-2-[2-[3-[trifluoromethyl]phenyl]ethyl]phenyl]-4,5-dihydro-4,4-dimethyloxazole, mp 63°–65°

(d) 2-[2-[2-[3-Chlorophenyl]ethyl]-3,4-dimethoxyphenyl]-4,5-dihydro-4,4-dimethyloxazole, mp 74°–76°

(e) 2-[3,4-Dimethoxy-2-[2-[3,5-dimethoxyphenyl]ethyl]-phenyl]-4,5-dihydro-4,4-dimethyloxazole, m/e 399

(f) 2-[3,4-Dimethoxy-2-[3-[3-methoxyphenyl]propyl]-phenyl]-4,5-dihydro-4,4-dimethyloxazole, m/e 383

(g) 2-[3,4-Dimethoxy-2-[4-[3-methoxyphenyl]butyl]-phenyl]-4,5-dihydro-4,4-dimethyloxazole, m/e 397

2. Preparation of benzoic acids (a) 3,4-Dimethoxy-2-[2-(3-methoxyphenyl)ethyl]benzoic acid A solution of the product from Intermediate 1 (a) (9.7 g) in excess methyl iodide (10 ml) was heated at reflux temperature for 4 hours. Dry ether (100 ml) was added and the resulting precipitate filtered to yield 11 g of the oxazolinium salt which was used without further purification.

A solution of this oxazolinium salt (11 g) in 20% aqueous sodium hydroxide (200 ml) and methanol (200 ml) was heated at reflux temperature for 6 hours. The cooled solution was acidified and the solid filtered, dried and crystallised from isopropanol to yield the title compound (6.2 g) as colourless prisms, mp 156°–158°.

Similarly prepared were:
(b) 3,4-Dimethoxy-2-[2-[3-methylphenyl]ethyl]benzoic acid, mp 150°–151°
(c) 3,4-Dimethoxy-2-[2-[3-trifluoromethyl]phenyl]ethyl]benzoic acid, mp 157°–159°
(d) 2-[2-[3-Chlorophenyl]ethyl]-3,4-dimethoxybenzoic acid, mp 155°–156°
(e) 2-[2-[3,5-Dimethoxyphenyl]ethyl]-3,4-dimethoxybenzoic acid, mp 158°–160°
(f) 3,4-Dimethoxy-2-[3-[3-methoxyphenyl]propyl]benzoic acid, mp 127°–128°
(g) 3,4-Dimethoxy-2-[4-[3-methoxyphenyl]butyl]benzoic acid, mp 118°–119°

3. Preparation of benzenemethanols (a) 3,4-Dimethoxy-2-[2-(methoxyphenyl)ethyl]benzenemethanol A solution of the product from step (b) (6.2 g) in dry tetrahydrofuran (50 ml) was stirred under an atmosphere of nitrogen during the addition of 40 ml of a 1M solution of borane in tetrahydrofuran complex. The mixture was heated under reflux for 3 hours, cooled and methanol (80 ml) added. The solution was evaporated to dryness, dissolved in ethyl acetate and washed with 2N hydrochloric acid, saturated sodium bicarbonate solution and brine. The organic phase was dried (MgSO₄) filtered and the solvent removed in vacuo to leave a solid which was crystallised from isopropanol to yield 5.2 g of the title compound as colourless flakes, mp 108°–109°.

Similarly prepared were:
(b) 3,4-Dimethoxy-2-[2-[3-methylphenyl]ethyl]benzenemethanol, mp 81°–83°
(c) 3,4-Dimethoxy-2-[2-[3-trifluoromethyl]phenyl]ethyl]benzenemethanol, mp 123°–125°
(d) 2-[2-[3-Chlorophenyl]ethyl]-3,4-dimethoxy benzenemethanol, mp 129°–131°
(e) 2-[2-[3,5-Dimethoxyphenyl]ethyl]-3,4-dimethoxy benzenemethanol, mp 125°–126°
(f) 3,4-Dimethoxy-2-[3-[3-methoxyphenyl]propyl]benzenemethanol, mp 62.5°–63.5°
(g) 3,4-Dimethoxy-2-[4-[3-methoxyphenyl]butyl]benzenemethanol, mp 54°–56°

4. Preparation of benezeneacetonitriles

Method A (a) 3,4-Dimethoxy-2-[2-(3-methoxyphenyl)ethyl]benzeneacetonitrile

A solution of the alcohol from step (c) (5 g) and thionyl chloride (1.5 ml) in dry dichloromethane (50 ml) was heated at reflux temperature for 3 hours. The solution was evaporated to dryness.

The cooled crude chloride was dissolved in dry dimethylsulphoxide (25 ml). Powdered sodium cyanide (1.5 g) was added to the solution and the mixture was stirred at 20° for 16 hours. Brine (150 ml) was added and the mixture extracted with ethyl acetate. The organic phase was washed with brine, dried over magnesium sulphate, filtered and evaporated on a steam bath until HCN had ceased to be evolved. Further evaporation gave a yellow solid which was crystallised from isopropanol to yield 4.0 g of the title compound as prisms, mp 98°–100°.

Similarly prepared were:
(b) 3,4-Dimethoxy-2-[2-[3-methylphenyl]ethyl]benzeneacetonitrile, mp 87°–88°
(c) 3,4-Dimethoxy-2-[2-[3-[trifluoromethyl]phenyl]ethyl]benzeneacetonitrile, mp 84°–85°
(d) 2-[2-[3-Chlorophenyl]ethyl]-3,4-dimethoxybenzeneacetonitrile, mp 71.5°–73.5°

Method B (a) 3,4-Dimethoxy-2-[3-[3-methoxyphenyl]propyl]benzeneacetonitrile

Methanesulphonylchloride (1.8 ml) was added to a cooled (−10°) stirred solution of the alcohol Intermediate 3 (f) (6.5 g), triethylamine (4 ml), 4-N,N-dimethylaminopyridine (5mg) in dry dichloromethane (50 ml). The mixture was stirred at room temperature under a nitrogen atmosphere for 2 hours. The solution was then washed with 2N hydrochloric acid, saturated sodium bicarbonate solution, brine, dried (MgSO₄), filtered and evaporated to leave the chloride as a yellow oil.

Powdered sodium cyanide (2 g) was added to a stirred solution of the chloride in dry dimethylsulphoxide (20 ml). The solution was stirred at room temperature for 16 hours. Brine (100 ml) was added and the mixture extracted with ethyl acetate. The organic phase was washed with brine, dried (MgSO₄), filtered and evaporated on a steam bath until HCN had ceased to be evolved. Further evaporation gave a solid which was purified by column chromatography (CH₂Cl₂:60/80 Petrol 1:2) as eluant and the revovered solid crystallised three times from isopropanol (3.95 g) to give the title compound, mp 78°–79°.

Similarly prepared were:
(b) 2-[2-[3,5-Dimethoxyphenyl]ethyl]-3,4-dimethoxybenzeneacetonitrile, m/e 341
(c) 3,4-Dimethoxy-2-[4-[3-methoxyphenyl]butyl]benzeneacetonitrile, m/e 339

5. Preparation of intermediates of formula VI (a) 3,4-Dimethoxy-2-[2-[3-methoxyphenyl]ethyl]benzeneethanamine hydrochloride A solution of the nitrile from step (d) (4 g) in dry tetrahydrofuran (50 ml) was stirred under an atmosphere of nitrogen during the addition of a 1M solution of borane in tetrahydrofuran (25.7 ml). The mixture was heated at reflux temperature for 2 hours. Methanol (40 ml) was added to the cooled reaction mixture and the solution evaporated to dryness. The residue was dissolved in methanol (50 ml) and conc. hydrochloric acid (5 ml) added. The mixture was heated at reflux temperature for 1 hour and then the solution was evaporated to dryness to yield a beige solid. This was treated with dilute sodium hydroxide solution to yield 3,4-dimethoxy-2-[2-(3-methoxyphenyl)ethyl-benzeneethanamine which was purified by flash column chromatography on silica gel using 90% chloroform/10% methanol as eluent. The resulting oil was treated with ethereal HCl to give 1.2 g of the title compound as colourless prisms after crystallisation from isopropanol, mp 164°–166°.

Similarly prepared were:
(b) 3,4-Dimethoxy-2-[2-[3-methylphenyl]ethyl]benzeneethanamine hydrochloride, mp 165.5°–166.5°

(c) 3,4-Dimethoxy-2-[2-[3-[trifluoromethyl]phenyl]ethyl]benzeneethanamine hydrochloride hydrate, mp 188°–190°
(d) 2-[2-[3-Chlorophenyl]ethyl]-3,4-dimethoxybenzeneethanamaine hydrochloride, mp 179°–181°
(e) 2-[2-[3,5-Dimethoxyphenyl]ethyl]-3,4-dimethoxybenzeneethanamine hydrochloride, mp 179°–180°
(f) 3,4-Dimethoxy-2-[3-[3-methoxyphenyl]propyl]benzeneethanamine hydrochloride, mp 88°–90°
(g) 3,4-Dimethoxy-2-[4-[3-methoxyphenyl]butyl]benzeneethanamine hydrochloride, oil 6. Preparation of intermediates of formula III from intermediates of formula VI and intermediates of formula VIII (a) N-[2-[3,4-Dimethoxy-2-[2-[3-methoxyphenyl]ethyl]phenyl]ethyl]-N'-[2-phenylethyl]hexane-1,6-diamide A solution of 6-oxo-6-(2-phenylethylamino)hexanoic acid (1.2 g) and N,N'-carbonyldiimidazole (0.77 g) in dry dichloromethane (50 ml) was stirred at 20° for 2 hours and a solution of 3,4-dimethoxy-2-[2-[3-methoxyphenyl]ethyl]benzeneethanamine (1.5 g) in dry dichloromethane (10 ml) was added. The mixture was stirred at 20° for 16 hours. Water (50 ml) was added and the organic phase was separated and washed with 2N hydrochloric acid, aqueous sodium bicarbonate and brine. The organic phase was dried (MgSO4), filtered and the solvent removed in vacuo. The resulting solid was crystallised from isopropanol to yield 2.1 g of the sub-title compound as colourless prisms, mp 150°–151°.

Similarly prepared were:
N-[2-[3,4-Dimethoxy-2-[2-[3-methoxyphenyl]ethyl]phenyl]ethyl]-N'-[2-phenylethyl]butane-1,4-diamide, mp 157°–158°.
(c) N-[2-[3,4-Dimethoxy-2-[2-[3-methoxyphenyl]ethyl]phenyl]ethyl]-N'-[2-phenylethyl]octane-1,8-diamide, mp 131°–133°.
(d) N-[2-Cyclohexylethyl]-N'-[2-[3,4-dimethoxy-2-[2-[3-methoxyphenyl]ethyl]phenyl]ethyl]hexane-1,6-diaminde, mp 136.5°–137.5°
(e) N-[2-[3,4-Dimethoxy-2-[2-[3-[trifluoromethyl]phenyl]ethyl]phenyl]ethyl]-N'-[2-phenylethyl]hexane-1,6-diamide, mp 165°–166°
(f) N-[2-[3,4-Dimethoxy-2-[2-[3-methylphenyl]ethyl]phenyl]ethyl]-N'-]2-phenylethyl]hexane-1,6-diamide, mp 169°–170°
(g) N-[2-[3,4-Dimethoxy-2-[2-[3-methylphenyl]ethyl]phenyl]ethyl]-N'-[2-[4-methoxyphenyl]ethyl]hexane-1,6-diamide, mp 265°–267°
(h) N-[2-[3,4-Dimethoxy-2-[3-[3-methoxyphenyl]propyl]phenyl]ethyl]-N'-[2-phenylethyl]hexane-1,6-diamide, mp 125°–126°
(i) N-[2-[3,4-Dimethoxy-2-[3-[3-methoxyphenyl]propyl]phenyl]ethyl]-N'-[2-[4-methoxyphenyl]phenylethyl]hexane-1,6-diamide, mp 145.5°–147.5°
(j) N-[2-[3,4-Dimethoxy-2-[2-[3,5-dimethoxyphenyl]ethyl]phenyl]ethyl]-N'-[2-phenylethyl]hexane-1,6-diamide, mp 167°–169°
(k) N-[2-[2-[2-[3-Chlorophenyl]ethyl]-3,4-dimethoxyphenyl]ethyl]-N'-[2-phenylethyl]hexane-1,6-diamide, mp 169°–170°
(l) N-[2-[2-[2-[3-Chlorophenyl]ethyl]-3,4-dimethoxyphenyl]ethyl]-N'-[2-[4-methoxyphenyl]ethyl]hexane-1,6-diamide, mp 164°–166°
(m) N-[2-Cyclohexylethyl]-N'-[2-[3,4-dimethoxy-2-[2-[4-methoxyphenyl]ethyl]phenyl]ethyl]hexane-1,6-diamide, mp 140.5°–143°
(n) N-[2-[3,4-Dimethoxy-2-[2-[4-methoxyphenyl]ethyl]phenyl]ethyl]-N'-[2-[4-methoxyphenyl]ethyl]hexane-1,6-diamide, mp 159°–160°
(o) N-[2-[3,4-Dimethoxy-2-[4-[3-methoxyphenyl]butyl]phenyl]ethyl]-N'-[2-phenylethyl]hexane-1,6-diamide, mp 123° ∝ 125°
(p) N-[2-[3,4-Dimethoxy-2-[2-[3-methoxyphenyl]ethyl]phenyl]ethyl]-N'-[2-[3,4-dimethoxyphenyl]ethyl]hexane-1,6-diamide, mp 141°–143°
(q) N-[2-[3,4-Dimethoxy-2-[2-[3-methoxyphenyl]ethyl]phenyl]ethyl]-N'-[2-[4-methoxyphenyl]ethyl]octane-1,8-diamide, mp 137°–139°
(r) N-[2-[3,4-Dimethoxy-2-[2-[3-methoxyphenyl]ethyl]phenyl]ethyl]-N'-[2-[3-methoxyphenyl]ethyl]hexane-1,6-diamide, mp 131°–132°
(s) N-[2-[3,4-Dimethoxy-2-[2-[3-methoxyphenyl]ethyl]phenyl]ethyl]-N'-[2-[4-methylphenyl]hexane-1,6-diamide, mp 157°–158°
(t) N-[2-[3,4-Dimethoxy-2-[2-[3-methoxyphenyl]ethyl]phenyl]ethyl]-N'-[2-[2,3-dimethoxyphenyl]ethyl]hexane-1,6-diamide, mp 134°–135°
(u) N-[2-[3,4-Dimethoxy-2-[2-[3-methoxyphenyl]ethyl]phenyl]ethyl]-N'-hexyl-hexane-1,6-diamide, mp 127°–128°
(v) N-[2-[3,4-Dimethoxy-2-[2-[3-methoxyphenyl]ethyl]phenyl]ethyl]-N'-[2-[2-fluoro-3,4-dimethoxyphenyl]ethyl]hexane-1,6-diamide, mp 140°–141°
(w) N-[2-[3,4-Dimethoxy-2-[2-[3-methoxyphenyl]ethyl]phenyl]ethyl]-N'-[2-[3-fluoro-4-methoxyphenyl]ethyl]hexane-1,6-diamide, mp 147°–149°
(x) E-N-[2-[3,4-Dimethoxy-2-[2-[3-methoxyphenyl]ethyl]phenyl]ethyl]-N'-[2-phenylethyl]-3-hexene-1,6-diamide, mp 131°–133°

7. Preparation of intermediates of formula IV from intermediates of formula VI and intermediates of formula VII (a) 6-[2-[3,4-Dimethoxy-2-[2-[3-methoxyphenyl]ethyl]phenyl]ethylamino]-6-oxo hexanoic acid Methyl 5-[chloroformyl]pentanoate (5.5 g) in dry dichloromethane (20 ml) was added dropwise to a stirred and cooled (−5° to 0°) solution of 3,4-dimethoxy[2-[2-[3-methoxyphenyl]ethyl]benzeneethanamine (9.64 g) and triethylamine (4.27 ml) in dry dichloromethane (150 ml). The resulting mixture was stirred at room temperature for 16 hours. The reaction mixture was washed with 2N hydrochloric acid (50 ml), 10% aqueous sodium bicarbonate solution (50 ml), water (50 ml), dried (MgSO4), and evaporated in vacuo affording the crude amido ester (14 g). A solution of the amido ester in methanol (125 ml) was treated with a solution of sodium hydroxide (1.35 g) in water (13.5 ml) and the mixture heated at reflux temperature for 3 hours. The cooled reaction mixture was acidified with 2N hydrochloric acid and extracted with chloroform (2×200 ml). The organic phase was separated, dried (MgSO4), filtered and evaporated to leave the title compound as a solid which crystallised from isopropanol as prisms (10.5 g), mp 119°–121°.

(b) 3-[2-[3,4-Dimethoxy-2-[2-[3-methoxyphenyl]ethyl]phenyl]ethylamino]-3-oxo-propylthioacetic acid A solution of 3-[methoxycarbonylmethylthio]propionic acid (1.97 g) and N,N'-carbonyldiimidazole (1.1 g) in dry dichloromethane (50 ml) was stirred under a nitrogen atmosphere for 1.5 hours. A solution of 3,4-dimethoxy-2-[2-[3-methoxyphenyl]ethyl]benzeneethanamine (3.49 g) in dry dichloromethane (40 ml) was added and the mixture stirred for 18 hours.

The solution was washed with 2N hydrochloric acid (100 ml), saturated sodium bicarbonate solution (100 ml) and brine (100 ml), dried (MgSO₄), filtered and evaporated to leave a dark brown oil. This oil was partially purified by flash chromatography (Merk 9385 silica gel) eluting with ether. Evaporation gave the methyl ester of the sub-title acid as an orange oil (2.43 g).

A solution of this oil in methanol (30 ml) was treated with water (7 ml) and saturated sodium bicarbonate solution (15 ml) and the mixture heated to reflux temperature under a nitrogen atmosphere for 3 hours. The majority of the methanol was removed in vacuo and the aqueous solution acidified and extracted with ether (3×50 ml). The organic phase was dried (MgSO₄), filtered and evaporated to give the title acid as a viscous yellow oil (1.92 g), MS M+ m/e 461.

8. Preparation of intermediates of formula III from intermediates of formula IV and formula V (a) N-[2-[3,4-Dimethoxy-2-[2-[3-methoxyphenyl]ethyl]-phenyl]ethyl]-N'-[2-[4-methoxyphenyl]ethyl]hexane-1,6-diamide A solution of the product from Intermediate 7(a) (2.09 g) and N,N-carbonyldiimidazole (0.77 g) in dry dichloromethane (100 ml) was stirred at 20° C. for 3 hours and a solution of 4-methoxybenzeneethanamine (0.72 g) in dry dichloromethane (10 ml) was then added. The mixture was stirred at 20° for 17 hours.

The solution was quenched with water (30 ml) and chloroform (100 ml) added. The organic phase was separated, dried (MgSO₄), filtered and evaporated to leave a solid which crystallised from isopropanol to give the title compound as a white solid 1.88 g, mp 153°–155°.

Similarly prepared were:
(b) N-[2-[4-Chlorophenyl]ethyl]-N'-[2-[3,4-dimethoxy-2-[2-[3-methoxyphenyl]ethyl]phenyl]ethyl]hexane-1,6-diamide, mp 150°–152°.
(c) N-[2,3-Dihydro-1H-inden-2-yl]-N'-[2-[3,4-dimethoxy-2-[2-[3-methoxyphenyl]ethyl]phenyl]ethyl]-hexane-1,6-diamide, mp 161°–162°.
(d) N-[2-[3,4-Dimethoxy-2-[2-[3-methoxyphenyl]ethyl]-phenyl]ethyl]-N'-[2-[4-nitrophenyl]ethyl]hexane-1,6-diamide, mp 128°–129°.
(e) N-[2-[3,4-Dimethoxy-2-[2-[3-methoxyphenyl]ethyl]-phenyl]ethyl]-N'-[2-[4-pyridyl]ethyl]hexane-1,6-diamide, mp 138°–141°.
(f) N-[2-[3,4-Dimethoxy-2-[2-[3-methoxyphenyl]ethyl]-phenyl]ethyl]-3-[2-oxo-2-[2-phenylethylamino]ethylthio]propanamide, as flakes from acetonitrile, mp 116°–118°

9. Preparation of intermediates of formula VIII (a) 6-(2-Cyclohexylethylamino)-6-oxohexanoic acid Methyl 5-[chloroformyl] pentanoate (4.2 g) in dry dichloromethane (20 ml) was added dropwise to a stirred solution of 2-cyclohexylethylamine (3 g) and triethylamine (3.3 ml) in dry dichloromethane (40 ml) under a N₂ atmosphere. The mixture was stirred at room temperature for 16 hours and heated under reflux for 1.5 hours.

The cooled solution was washed with 2N hydrochloric acid, saturated bicarbonate solution and brine. The organic solution was dried (MgSO₄), filtered and evaporated to leave the ester as a yellow oil (6.3 g).

A solution of the ester in methanol (50 ml) and 10% sodium hydroxide solution (10 ml) was heated under reflux for 3 hours. The solution was evaporated to half volume and acidified with 2N hydrochloric acid. The precipitate was extracted with ethyl acetate and the solution dried (MgSO₄), filtered and evaporated. Crystallisation from ethyl acetate gave the title acid as a colourless solid (3 g), mp 95°–96°.

Similarly prepared were:
(b) 8-[2-[4-Methoxyphenyl]ethylamino]-8-oxooctanoic acid, mp 125.1°–125.9°
(c) 6-[2-[3-Methoxyphenyl]ethylamino]-6-oxohexanoic acid, mp 96°–98°
(d) 6-[2-[4-Methylphenyl]ethylamino]-6-oxohexanoic acid, mp 143°–144°
(e) 6-Hexylamino-6-oxohexanoic acid, mp 95°–96°
(f) 6-[2-[3-Fluoro-4-methoxyphenyl]ethylamino]-6-oxohexanoic acid, mp 118°–120°
(g) 6-[2-[2-Fluoro-3,4-dimethoxyphenyl]ethylamino]-6-oxohexanoic acid, mp 95°–97°
(h) 6-[2-[2,3-Dimethoxyphenyl]ethylamino]-6-oxohexanoic acid, m/e 309
(i) 6-Oxo-6-[2-phenylethylamino]-3,E-hexenoic acid Ethylchloroformate (11.25 ml) was added to a stirred solution of trans 3-hexenedioc acid (16.93 g) and triethylamine (16.35 ml) in dry chloroform (170 ml) at −5° under a N₂ atmosphere. The solution was stirred for 30 minutes then a solution of 2-phenylethylamine (14.78 ml) in dry chloroform (50 ml) was added. The reaction mixture was stirred at room temperature for 3 hours. The solution was washed with 2N hydrochloric acid, saturated sodium bicarbonate solution, brine, dried (MgSO₄), filtered and evaporated to leave the title compound as a solid which crystallised from isopropanol (8.73 g), mp 101°–103°.

10. Preparation of intermediates of formula II (a) N-[2-[3,4-Dimethoxy-2-[2-[3-methoxyphenyl]ethyl]-phenyl]ethyl]-N'-[2-phenylethyl]hexane-1,6-diamine dihydrochloride A solution of the product from Intermediate 6(a) (1.8 g) in dry tetrahydrofuran (80 ml) was stirred under an atmosphere of nitrogen during the addition of a 1M solution of borane in tetrahydrofuran (16 ml). The mixture was heated at reflux temperature for 4 hours and then stirred at 20° for 16 hours. Methanol (50 ml) was added to the cooled solution and the mixture evaporated to dryness. The residue was dissolved in methanol (50 ml) and concentrated hydrochloric acid (5 ml) added. The mixture was heated at reflux temperature for 1 hour. The solution was evaporated to give a solid which was crystallised from ethanol to yield 1.6 g of the dihydrochloride salt of the title compound as colourless prisms, mp 229°–231°.

Similarly prepared were:
(b) N-[2-[3,4-Dimethoxy-2-[2-[3-methoxyphenyl]ethyl]-phenyl]ethyl]-N'-[2-phenylethyl]butane-1,4-diamine, dihydrochloride, mp 213°–215°
(c) N-[2-[3,4-Dimethoxy-2-[2-[3-methoxyphenyl]ethyl]-phenyl]ethyl]-N'-[2-phenylethyl]octane-1,8-diamine, dihydrochloride, mp 219°–220°
(d) N-[2-[3,4-Dimethoxy-2-[2-[3-methoxyphenyl]ethyl]-phenyl]ethyl]-N'-[2-[4-methoxyphenyl]ethyl]hexane-1,6-diamine dihydrochloride, mp 223°–226°
(e) N-[2-[4-Chlorophenyl]ethyl]-N'-[2-[3,4-dimethoxy-2-[2-[3-methoxyphenyl]ethyl]phenyl]ethyl]hexane-1,6-diamine dihydrochloride, mp 225°–227°.
(f) N-[2,3-Dihydro-1H-inden-2-yl]-N'-[2-[3,4-dimethoxy-2-[2-[3-methoxyphenyl]ethyl]phenyl]ethyl]-hexane-1,6-diamine dihydrochloride, mp 229°–231°.

(g) N-[2-Cyclohexylethyl]-N'-[2-[3,4-dimethoxy-2-[2-[3-methoxyphenyl]ethyl]phenyl]ethyl]hexane-1,6-diamine dihydrochloride, mp 227°–228°.

(h) N-[2-[3,4-Dimethoxy-2-[2-[3-methoxyphenyl]ethyl]phenyl]ethyl]-N'-[2-[4-nitrophenyl]ethyl]hexane-1,6-diamine dihydrochloride, mp 197°–198°.

(i) N-[2-[3,4-Dimethoxy-2-[2-[3-methoxyphenyl]ethyl]phenyl]ethyl]-N'-[2-[4-pyridyl]ethyl]hexane-1,6-diamine dihydrochloride, mp 192°–194°.

(j) N-[2-[3,4-Dimethoxy-2-[2-[3-methoxyphenyl]ethyl]phenyl]ethyl]-3-[2-[2-phenylethylamino]ethylthio]-propanamine, dihydrochloride, prisms from isopropanol, mp 186°–188°

(k) N-[2-[3,4-Dimethoxy-2-[2-[3-methylphenyl]ethyl]phenyl]ethyl]-N'-[2-phenylethyl]hexane-1,6-diamine dihydrochloride, mp 241°–243°

(l) N-[2-[3,4-Dimethoxy-2-[2-[2-[3-trifluoromethyl]phenyl]ethyl]phenyl]ethyl]-N'-[2-phenylethyl]hexane-1,6-diamine dihydrochloride, mp 223°–226°

(m) N-[2-[3,4-Dimethoxy-2-[2-[2-[3-methylphenyl]ethyl]phenyl]ethyl]-N'-[2-[4-methoxyphenyl]ethyl]-hexane-1,6-diamine dihydrochloride, mp 233°–235°

(n) N-[2-[3,4-Dimethoxy-2-[3-[3-methoxyphenyl]propyl]phenyl]ethyl]-N'-[2-phenylethyl]hexane-1,6-diamine dihydrochloride, mp 171°–172°

(o) N-[2-[3,4-Dimethoxy-2-[3-[3-methoxyphenyl]propyl]phenyl]ethyl]-N'-[2-[4-methoxyphenyl]ethyl]-hexane-1,6-diamine dihydrochloride, mp 162°–164°

(p) N-[2-[3,4-Dimethoxy-2-[2-[3,5-dimethoxyphenyl]ethyl]phenyl]ethyl]-N'-[2-phenylethyl]hexane-1,6-diamine dihydrochloride, mp 224°–226°

(q) N-[2-[3,4-Dimethoxy-2-[2-[3-methoxyphenyl]ethyl]phenyl]ethyl]-N'-[2-[3,4-dimethoxyphenyl]ethyl]hexane-1,6-diamine dihydrochloride, mp 205°–207°

(r) N-[2-[3,4-Dimethoxy-2-[2-[3-methoxyphenyl]ethyl]phenyl]ethyl]-N'-[2-[4-methoxyphenyl]ethyl]octane-1,8-diamine dihydrochloride, mp 227°–229°

(s) N-[2-[3,4-Dimethoxy-2-[2-[3-methoxyphenyl]ethyl]phenyl]ethyl]-N'-[2-[3-methoxyphenyl]ethyl]hexane-1,6-diamine dihydrochloride, mp 193°–195°

(t) N-[2-[3,4-Dimethoxy-2-[2-[3-methoxyphenyl]ethyl]phenyl]ethyl]-N'-[2-[4-methylphenyl]hexane-1,6-diamine dihydrochloride, mp 218°–220°

(u) N-[2-[3,4-Dimethoxy-2-[2-[3-methoxyphenyl]ethyl]phenyl]ethyl]-N'-[2-[2,3-dimethoxyphenyl]ethyl]hexane-1,6-diamine dihydrochloride, mp 201.5°–202.5°

(v) N-[2-[3,4-Dimethoxy-2-[2-[3-methoxyphenyl]ethyl]phenyl]ethyl]-N'-hexyl hexane-1,6-diamine dihydrochloride, mp 194°–196°

(w) N-[2-[3,4-Dimethoxy-2-[2-[3-methoxyphenyl]ethyl]phenyl]ethyl]-N'-[2-[3-fluoro-3,4-dimethoxyphenyl]ethyl]-hexane-1,6-diamine dihydrochloride, mp 182°–184°

(x) N-[2-[3,4-Dimethoxy-2-[2-[3-methoxyphenyl]ethyl]phenyl]ethyl]-N'-[2-[3-fluoro-4-methoxyphenyl]ethyl]hexane-1,6-diamine dihydrochloride, mp 200°–202°

(y) N-[2-[2-[2-[3-Chlorophenyl]ethyl]-3,4-dimethoxyphenyl]ethyl]-N'-[2-phenylethyl]hexane-1,6-diamine dihydrochloride, mp 246°–247°

(z) N-[2-[2-[2-[3-Chlorophenyl]ethyl]-3,4-dimethoxyphenyl]ethyl]-N'-[2-[4-methoxyphenyl]hexane-1,6-diamine dihydrochloride, mp 238°–240°

(aa) N-[2-Cyclohexylethyl]-N'-[2-[3,4-dimethoxy-2-[2-[4-methoxyphenyl]ethyl]phenyl]ethyl]hexane-1,6-diamine dihydrochloride, mp 225.5°–226.5°

(bb) N-[2-[3,4-Dimethoxy-2-[2-[4-methoxyphenyl]ethyl]phenyl]ethyl]-N'-[2-[4-methoxyphenyl]ethyl]-hexane-1,6-diamine dihydrochloride, mp 198°–199°

(cc) N-[2-[3,4-Dimethoxy-2-[4-[3-methoxyphenyl]butyl]phenyl]ethyl]-N'-[2-phenylethyl]hexane-1,6-diamine dihydrochloride, mp 215°–217°

(dd) E-N-[2-[3,4-Dimethoxy-2-[2-[3-methoxyphenyl]ethyl]phenyl]ethyl]-N'-[2-phenylethyl]-3-hexene-1,6-diamine dihydrochloride, mp 212°–216°

(ee) N-[4-[2-[6-[2-[3,4-Dimethoxy-2-[2-[3-methoxyphenyl]ethyl]phenyl]ethylamino]hexylamino]ethyl]phenyl]methanesulphonamide dihydrochloride, mp 277°–279°

11.

N-2-[3,4-Dimethoxy-2-[3-methoxyphenyl]ethyl]-3-[2-[2-phenylethylamino]ethanesulphonyl]propanamine A solution of trifluoroacetic anhydride (6 ml) in dry dichloromethane (40 ml) was added dropwise to a stirred solution of Intermediate 10(j) (6.45 g) and triethylamine (4.5 ml) in dry dichloromethane (120 ml). The mixture was stirred for 16 hours then washed with 2N hydrochloric acid, saturated sodium bicarbonate solution and water, dried (MgSO$_4$), filtered and evaporated to give the bis-trifluoroacetyl derivative as a viscous oil (8 g).

A solution of the bis-trifluoroacetyl derivative (4 g) in dry dichloromethane (100 ml) was cooled to −10° and treated with stirring with m-chloroperoxybenzoic acid (3.0 g). The mixture was allowed to warm to room temperature and stirred for 4 hours. The solution was washed with saturated sodium bicarbonate solution and water, dried (MgSO$_4$), filtered and evaporated. Purification by flash chromatography (Merck 9385 silica gel) eluting with ethyl acetate/40:60 petrol (2:1) and then ethyl acetate gave the trifluoroacetyl derivative of the title compound as a yellow oil (3.3 g).

A solution of this oil in methanol (70 ml) containing anhydrous potassium carbonate (1.32 g) and water (10 ml) was heated to reflux temperature in a nitrogen atmosphere for 3 hours. The methanol was removed under vacuum and the aqueous residues extracted with chloroform. The organic solution was dried (MgSO$_4$), filtered and evaporated to leave an oil which gave a white precipitate on treatment with ethereal/HCl (20 ml). The filtered solid crystallised from ethanol to give the sesquihydrate of the hydrochloride of the title compound as prisms (0.8), mp 166.3°–168.5°.

12.

N-[2-[4-Aminophenyl]ethyl]-N'-[2-[3,4-dimethoxy-2-[2-[3-methoxyphenyl]ethyl]phenyl]ethyl]hexane-1,6-diamine trihydrochloride hemihydrate A solution of Intermediate 10(h) (1.4 g) in dry methanol (100 ml) was hydrogenated at atmospheric pressure and room temperature over a platinum oxide catalyst (0.23 g) for 4 hours. The catalyst was filtered off and the solution evaporated to give the title compound as a solid which crystallised from ethanol (1.05 g), mp 211°–214°.

13.

N-[2-[4-[Methanesulphonyl]aminophenyl]ethyl]-N'-[2-[3,4-dimethoxy-2-[2-[3-methoxyphenyl]ethyl]phenyl]ethyl]hexane-1,6-diamide (a) N-[2-[4-Aminophenyl]ethyl]-N'-[2-[3,4-dimethoxy-2-[2-[3-methoxyphenyl]ethyl]phenyl]ethyl]hexane-1,6-diamide A solution of Intermediate 8(d) (3.6 g) in dry methanol (150 ml) and dry ethanol (100 ml) was hydrogenated over a platinum oxide catalyst at atmospheric pressure and room temperature for 4 hours. The catalyst was filtered and the filtrate evaporated to leave the sub-title compound as a colourless solid (3.5 g), mp 163°–165°.

(b) N-[2-[4-[Methanesulphonyl]aminophenyl]ethyl]-N'-[2-[3,4-dimethoxy-2-[2-[3-methoxyphenyl]ethyl]-phenyl]ethyl]hexane-1,6-diamide Methanesulphonylchloride (0.41 ml) was added to a stirred solution of the Intermediate (a) (2.74 g) and triethylamine (0.74 ml) in dry dimethylformamide. The solution was stirred at room temperature for 10 hours.

The solution was poured onto brine and extracted with ethyl acetate. The organic phase was washed with 2N hydrochloric acid, brine, dried (MgSO$_4$), filtered and evaporated to give a red solid which crystallised from isopropanol to give the title compound as a pink solid (1.72 g), mp 157°–159°.

14. Preparation of
3-[2-[3-Hydroxyphenyl]ethyl]-4-[2-[6-[2-phenylethoxy]-hexylamino]ethyl]-1,2-benzenediol (a)  2-[2-[3-(phenylmethoxy)phenyl]ethyl]-3,4-bis(-phenylmethoxy) benzeneacetonitrile.

To the 2-[2-[(3-methoxyphenyl)ethyl]-3,4-dimethoxybenzeneacetonitrile (5 g) in dichloromethane (100 ml) at −78°, under nitrogen was added 1M boron tribromide (80 ml) in dichloromethane. The reaction was then stirred at room temperature for 4 hours. Ice/water (50 ml) was added and the aqueous extracted with ether. The ethereal layer was dried (MgSO$_4$) and concentrated to give a purple oil. This oil was dissolved in dry dimethylformamide (100 ml) and then potassium carbonate (22.18 g) followed by benzyl bromide (16.5 g) were added. The reaction was stoppered and stirred at room temperature for 14 hours. Ice/water was added, the aqueous layer extracted with ether, the ethereal layer washed with brine, dried (MgSO$_4$) and concentrated to give a yellow oil. This was purified by flash column chromatography on silica gel using ether:petroleum ether 40°–60°; 1:2; v/v to give 2.6 g of the sub-title compound as a white solid, mp 90° (softens-)—95°–97° melts.

(b) 3,4-Bis(phenylmethoxy)-2-[2-(3-(phenylmethoxy)-phenyl)ethyl]phenylethylamine hydrochloride To the nitrile (3 g) from step (a) in dry tetrahydrofuran (100 ml) under nitrogen was added 1M borane in tetrahydrofuran (10 ml). The mixture was heated under reflux for 3 hours. Methanol (40 ml) was added to the cooled reaction mixture and the solution evaporated to dryness. The residue was dissolved in methanol (150 ml) and concentrated hydrochloric acid (15 ml) added. The mixture was heated under reflux for 1 hour and then the solution was evaporated to dryness to yield a white solid. Recrystallisation from isopropanol gave 2 g of the sub-title compound as a white solid, mp 212°–214°.

(c)
N-(2-(2-(3-(Phenylmethoxy)phenylethyl)-3,4-bis(-phenylmethoxy)phenyl)ethyl)-2,2,2-trifluoroaceamide To the amine hydrochloride (2 g) from step (b) in dichloromethane (100 ml) was added triethylamine (0.66 g) followed by trifluoroacetic anhydride (0.68 g) and N,N-dimethylaminopyridine (10 mg). The reaction mixture was stirred at room temperature for 14 hours. Chloroform was added to the reaction, the organic layer was separated and then washed with 2N hydrochloric acid, saturated sodium bicarbonate solution, brine, dried (MgSO$_4$) and evaporated to give a white solid. Recrystallisation from ether/petroleum ether 40°–60° gave the sub-title compound (1.6 g) as white prisms, mp 142°–144°.

(d)
N-[6-(2-Phenylethoxy)hexyl]-N-(2-(2-(3-(phenylmethoxy)phenylethyl-3,4-bis(phenylmethoxy)phenylethyl-2,2,2-trifluoroacetamide The trifluoroacetamide (1.6 g) from step (d) in dry dimethylformamide (20 ml) was added to a stirred suspension of NaH (80 mg, oil-free) in dry dimethylformamide (15 ml) under nitrogen. The mixture was stirred at 70° for 1.5 hours. 2-(6-bromohexyloxy)-1-phenylethane (0.8 g) in dry dimethylformamide (10 ml) was then added dropwise and the reaction stirred at room temperature for 14 hours. The solvent then removed, 2N hydrochloric acid (30 ml) was added and the aqueous extracted with ethyl acetate. The ethyl acetate layer was washed with brine, dried (MgSO$_4$) and concentrated to give an oil. The oil was purified by column chromatography (silica, petroleum ether 40°–60°:ether, 3:2, v/v) to give the sub-title compound as a colourless oil (0.6 g), m/e 855 (MH+).

(e) N-[6-(2-Phenylethoxy)hexyl]-N-(2-(2-(b 3-(phenylmethoxy)phenylethyl)-3,4-bis(phenylmethoxy)phenylethylamine hydrochloride The amide from step (d) (0.6 g) in methanol (25 ml) and sodium hydroxide (60 mg) in water (10 ml) was refluxed for 3 hours, Methanol was removed in vacuo and the aqueous extracted with ethyl acetate to give an oil. This oil was purified by column chromatography (silica; CHCl$_3$MCOH; 9:1; v/v) to give the product as an oil. The oil was taken up in ether, ethereal hydrogen chloride was added to give a white solid which was filtered off and dried to give the hydrochloride salt of the title compound (100 mg), mp 151°–153°.

B. Examples

Example 1

3-[2-[3-Hydroxyphenyl]ethyl]-4-[2-[6-[2-phenylethylamino]hexylamino]ethyl]-1,2-benzenediol A solution of the diamine Intermediate 10 (a) (1.4 g) in 48% aqueous hydrobromic acid (20 ml) containing hypophosphorous acid (0.1 ml) was heated at reflux temperature for 3 hours under an atmosphere of nitrogen. The solution was evaporated to dryness and the residue treated with ethyl acetate. The dihydrobromide salt of the title compound (1.3 g) was filtered off as a beige solid and dried at 80° under vacuum, mp 167°–170°.

Example 2

3-[2-[3-Hydroxyphenyl]ethyl]-4-[2-[4-[2-phenylethylamino]butylamine]ethyl]-1,2-benzenediol A solution of Intermediate 10 (b) (1.1 g) in concentrated hydrochloric acid (100 ml) was heated under reflux under a nitrogen atmosphere for 5 days. The solution was evaporated to dryness and the residue crystallised from isopropanol/ether as the dihydrochloride hydrate of the title compound (0.8 g), mp presoftens 132–134, mp 170°.

Example 3

3-[2-[3-Hydroxyphenyl]ethyl]-4-[2-[8-[2-phenylethylamino]octylamino]ethyl]-1,2-benzenediol A solution of 1M boron tribromide in dichloromethane (60 ml) was added dropwise to a cooled (−78°) suspension of Intermediate 10 (c) (0.617 g) in dry dichloromethane (40 ml). The mixture was stirred at room temperature under a $N_2$ atmosphere for 4 hours, then methanol (20 ml) added and the mixture evaporated to leave a solid which recrystallised from ethanol/ether to give prisms of the dihydrobromide hydrate title compound (0.58 g), mp 175°–177°.

Example 4

The following compound was prepared from the corresponding Intermediate 10, by the method of Example 1:

4.1 4-[2-[6-[2-Cyclohexylethylamino]hexylamino]ethyl]-3-[2-[3-hydroxyphenyl]ethyl]-1,2-benzenediol as a dihydrobromide salt, mp 172.5°–174.5°.

4.2 3-[2-[3-Hydroxyphenyl]ethyl]-4-[2-[6-[2-[4-methylphenyl]ethylamino]hexylamino]ethyl]-1,2-benzenediol as a diihydrobromide, mp 170°–172° decomposes.

4.3 3-[2-[3-Hydroxyphenyl]ethyl]-4-[2-[6-[2-[3-hydroxyphenyl]ethylamino]hexylamino]ethyl]-1,2-benzenediol as a dihydrobromide, mp 158°–160°.

4.4 4-[2-[6-[6-Hexylamino]hexylamino]ethyl]-3-[2-[3-hydroxyphenyl]ethyl]-1,2-benzenediol as a dihydrobromide, mp 151°–153°.

Example 5

The following compounds were prepared from the corresponding Intermediate 10, by the method of Example 2:

5.1 4-[2-[6-[2-[4-Chlorophenyl]ethylamino]hexylamino]ethyl]-3-[2-[3-hydroxyphenyl]ethyl]-1,2-benzenediol, as a dihydrochloride, hydrate, as prisms, mp softens at 123°, melts at 184°–187°.

5.2 4-[2-[6-[2,3-Dihydro-1H-indene-2-yl amino]hexylamino]ethyl]-3-[2-[3-hydroxyphenyl]ethyl]-1,2-benzenediol, as dihydrochloride hydrate, mp presoftens 108°, melts at 127°–132°.

5.3 3-[2-[3-Hydroxyphenyl]ethyl]-4-[2-[6-[2-[4-pyridyl]ethylamino]hexylamino]ethyl]-1,2-benzenediol, as a trihydrochloride, hydrate, mp softens 137°, decomposes 180°–189°.

5.4 3-[2-[3-Hydroxyphenyl]ethyl]-4-[2-[6-[2-phenylethylamino]hexylamino]ethyl]-1,2-benzenediol as a dihydrochloride 206°–208°.

Low melting dihydrochloride also isolated from ethanol, mp 141°–144°.

Example 6

The following compounds were prepared from the corresponding Intermediates 10, 11, 12, 13 or 14 by the method of Example 3:

6.1 3-[2-[3-Hydroxyphenyl]ethyl]-4-[2-[6-[2-[4-hydroxyphenyl]ethylamino]hexylamino]ethyl]-1,2-benzenediol, as a dihydrobromide hydrate, mp softens at 85°. melts at 135°–140°.

6.2 3-[2-[3-Hydroxyphenyl]ethyl]-4-[2-[3-[2-[2-phenylethylamino]ethylthio]propylamino]ethyl]-1,2-benzenediol, as a dihydrobromide, colourless prisms, mp 122°–124°.

6.3 3-[2-[3-Hydroxyphenyl]ethyl]-4-[2-[3-[2-[2-phenylethylamino]ethanesulphonyl]propanylamino]ethyl]-1,2-benzenediol, as a dihydrobromide hydrate, mp softens 96°–98°, mp 195°–198°.

6.4 3-[2-[3-Hydroxyphenyl]ethyl]-4-[2-[6-[2-[4-nitrophenyl]ethylamino]hexylamino]ethyl]-1,2-benzenediol, as a dihydrobromide hydrate, mp 85°–130° decomposes 6.5 4-[2-[6-[2-[4-Aminophenyl]ethylamino]hexylamino]ethyl]-3-[2-[3-hydroxyphenyl]ethyl]-1,2-benzenediol, as a trihydrobromide, mp 218°–220°.

6.6 4-[2-[6-[2-[3,4-Dihydroxy-2-[2-[3-hydroxyphenyl]ethyl]phenyl]ethylamino]hexylamino]ethyl]-3-fluoro-1,2-benzenediol as a dihydrobromide hydrate, mp 90°–92° dec 6.7 4-[2-[6-[2-[3-[Fluoro-4-hydroxyphenyl]ethylamino]hexylamino]ethyl]-3-[2-[3-hydroxyphenyl]ethyl]-1,2-benzenediol as a dihydrobromide hydrate, mp 88°–90° dec 6.8 3-[2-[3-Methylphenyl]ethyl[-4-[2-[6-[2-phenylethylamino]hexylamino]ethyl]-1,2-benzenediol as a dihydrobromide from isopropanol, mp 169°–171°

6.9 4-[2-[6-[2-[4-Hydroxyphenyl]ethylamino]hexylamino]ethyl]3-[2-[3-methylphenyl]ethyl]-1,2-benzenediol as a dihydrobromide from isopropanol, mp 196°–198°

6.10 3-[2-[3-Hydroxyphenyl]ethyl]-4-[2-[8-[2-[4-hydroxyphenyl]ethylamino]hexylamino]ethyl]-1,2-benzenediol as a dihydrobromide, mp 217°–219°

6.11 4-[2-[6-[b 2-Phenyl]ethylamino]hexylamino]ethyl]-3-[2-[3-[trifluoromethyl]phenyl]ethyl]-1,2-benzenediol as a dihydrobromide from ethanol/ether, mp softens 103°–105° melts 145°–146° dec 6.12 3-[2-[3,5-Dihydroxyphenyl]ethyl]-4-[2-[6-[2-phenylethylamino]hexylamino]ethyl]-1,2-benzenediol as a dihydrobromide hydrate, mp softens 68°–70° melts 112°–115°

6.13 4-[2-[6-[2-[3,4-Dihydroxyphenyl]ethylamino]hexylamino]ethyl]-3-[2-[3-hydroxyphenyl]ethyl]-1,2-benzenediol as a dihydrobromide hydrate, mp 167°–169°

6.14 3-[3-[3-Hydroxyphenyl]propyl]-4-[2-[6-[2-phenylethylamino]hexylamino]ethyl]-1,2-benzenediol as a dihydrobromide, hydrate melts 77°–79° decomposes 6.15 3-[3-[3-Hydroxyphenyl]propyl]-4-[2-[6-[2-[4-hydroxyphenyl]ethylamino]hexylamino]ethyl]-1,2-benzenediol as a dihydrobromide hydrate, mp 92°–94° decomposes 6.16 4-[2-[6-[2-[2,3-Dihydroxyphenyl]ethylamino]hexylamino]ethyl]-3-[2-[3-hydroxyphenyl]ethyl]-1,2-benzenediol as a dihydrobromide 6.17 3-[2-[3-Chlorophenyl]ethyl]-4-[2-[2-[6-[2-phenylethylamino]hexylamino]ethyl]-1,2-benzenediol as a dihydrobromide from ethanol, mp 188°–190°

6.18 3-[2-[3-Chlorophenyl]ethyl]-4-[2-[6-[2-[4-hydroxyphenyl]ethylamino]hexylamino]ethyl]-1,2-benzenediol as a dihydrobromide, mp 206°–208°

6.19 4-[2-[6-[2-Cyclohexylethylamino]hexylamino]ethyl]-3 -[2-[4-hydroxyphenyl]ethyl]-1,2-benzenediol as a dihydrobromide. mp 194 -195°

6.20 3-[2-[4-Hydroxyphenyl]ethyl]-4-[2-[6-[2-[4-hydroxyphenyl]ethylamino]hexylamino]ethyl]-1,2-benzenediol as a dihydrobromide, mp 98°–101°

6.21 3-[4-[3-Hydroxyphenyl]butyl]-4-[2-[6-[2-phenylethylamino]hexylamino]ethyl]-1,2-benzenediol as a dihydrobromide, hydrate mp 72°–74° decomposes 6.22 3-[2-[3-Hydroxyphenyl]ethyl]-4-[2-[6-[2-[4-pyridyl]ethylamino]hexylamino]ethyl]-1,2-benzenediol as a trihydrobromide hydrate softens 180°, melts 189°–190°

6.23 E-3-[2-[3-Hydroxyphenyl]ethyl]-4-[2-[6-[2-phenylethylamino]hexylamino]ethyl]-3-hexenylamino]-1,2-benzenediol as a dihydrobromide. m/e FAB 475 (+1)

6.24 N-[4-[2-[6-[2-[3,4-Dihydroxy-2-[2-[3-hydroxyphenyl]ethyl]phenyl]ethylamino]hexylamino]ethyl]phenyl]methanesulphonamide dihydrobromide, mp softens 76°–78°, melts 146°–149°

Example 7

4-[2-[6-(2-Phenylethoxy)]hexylamino]ethyl-3-[2-[3-hydroxypehnyl]ethyl]-1,2-benzenediol The Intermediate from A 14 (e) (100 g) was dissolved in dry ethanol (50 ml) and then hydrogenated over 10% palladium on carbon (25 mg). The catalyst was removed by filtration and the filtrate concentrated in vacuo to give the hydrochloride salt of the title compound as a glassy solid (60 mg), m/e M+478 (+1).

We claim:
1. A compound of formula I,

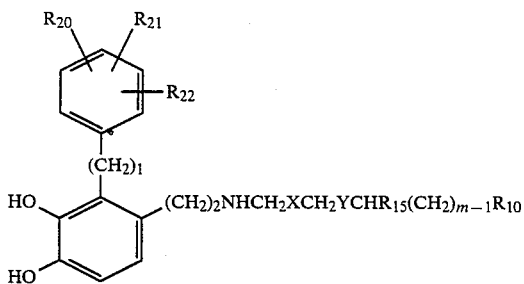

in which X represents a C2 to 8 alkylene chain optionally interrupted by a double bond or by $S(O)_n$, wherein n is 0, 1 or 2;

Y represents O or NH, l and m each independently represent 2, 3 or 4, $R_{10}$ represents phenyl substituted by one or more substituents $R_{23}$, which may be the same or different; or $R_{10}$ represents pyridyl, a saturated carbocyclic group, alkyl C 1 to 6 or hydrogen, $R_{15}$ represents hydrogen or together with $R_{23}$ forms a $(CH_2)_p$ chain, wherein p represents 0, 1 or 2;

$R_{20}$, $R_{21}$, $R_{22}$ and $R_{23}$, which may be the same or different, independently represent hydrogen, alkyl C 1 to 6, $NHR_{25}$, SH, $NO_2$, halogen, $CF_3$, $SO_2R_{30}$, $CH_2OH$ or OH, wherein $R_{25}$ represents hydrogen, alkyl C 1 to 6, alkanoyl C 1 to 6 or $SO_2$ alkyl C 1 to 6, and $R_{30}$ represents alkyl C 1 to 6 or $NH_2$, provided that thwn X represents an uninterrupted C4 alkylene chain, Y represents NH, m represents 2, l represents 2, $R_{10}$ represents phenyl, $R_{15}$ represents hydrogen, and $R_{21}$, $R_{22}$ and $R_{23}$ represent hydrogen, then $R_{20}$ does not represent hydrogen or 4-OH, and pharmaceutically acceptable salts and solvates thereof.

2. A compound according to claim 1, wherein $R_{10}$ represents phenyl substituted by one or more substituents $R_{23}$, which may be the same or different.

3. A compound according to claim 1, wherein $R_{23}$ independently represents one or more of hydrogen, halogen, hydroxy, $NH_2$, $NHSO_2$alkyl C 1 to 6, $NO_2$ or alkyl C 1 to 6.

4. A compound according to claim 1, wherein $R_{20}$, $R_{21}$ and $R_{22}$ independently represent hydrogen, hydroxy, alkyl C 1 to 6, halogen or trifluoromethyl.

5. A compound according to claim 1, wherein one of $R_{20}$, $R_{21}$ or $R_{22}$ represents 3-OH.

6. A compound according to claim 1, wherein Y represents NH.

7. A compound according to claim 1, which is 3-[2-[3-Hydroxyphenyl]ethyl]-4-[2-[6-[2-phenylethylamino]hexylamino]ethyl]-1,2-benzenediol, or a pharmaceutically acceptable salt or solvate thereof.

8. A compound according to claim 1, which is 3-[2-[3-Hydroxyphenyl]ethyl]-4-[2-[4-[2-phenylethylamino]butylamino]ethyl]-1,2-benzenediol 3-[2-[3-Hydroxyphenyl]ethyl]-4-[2-[8-[2-phenylethylamino]octylamino]ethyl]-1,2-benzenediol 4-[2-[6-[2-Cyclohexylethylamino]hexylamino]ethyl]-3-[2-[3-hydroxyphenyl]ethyl]-1,2-benzenediol 3-[2-[3-Hydroxyphenyl]ethyl]-4-[2-[6-[2-[4-methylphenyl]ethylamino]hexylamino]ethyl]-1,2-benzenediol 3-[2-[3-Hydroxyphenyl]ethyl]-4-[2-[2-[6-[2-[3-hydroxyphenyl]ethylamino]hexylamino]ethyl]-1,2-benzenediol 4-[2-[6-hexylamino]ethyl]-3-[2-[3-hydroxyphenyl]ethyl]-1,2-benzenediol 4-[2-[6-[2-[4-Chlorophenyl]ethylamino]hexylamino]ethyl]-3-[2-[3-hydroxyphenyl]ethyl]-1,2-benzenediol 4-[2-[6-[2,3-Dihydro-1H-indene-2-yl amino]hexylamino]ethyl]-3-[2-[3-hydroxyphenyl]ethyl]-1,2-benzenediol 3-[2-[3-Hydroxyphenyl]ethyl]-4-[2-[6-[2-[4-pyridyl]ethylamino]hexylamino]ethyl]-1,2-benzenediol 3-[2-[3-Hydroxyphenyl]ethyl]-4-[2-[6-[2-phenylethylamino]hexylamino]ethyl]-1,2-benzenediol 3-[2-[3-Hydroxyphenyl]ethyl]-4-[2-[6-[2-[4-hydroxyphenyl]ethylamino]hexylamino]ethyl]-1,2-benzenediol 3-[2-[3-Hydroxyphenyl]ethyl]-4-[2-[3-[2-[2-phenylethylamino]ethylthio]propylamino]ethyl]-1,2-benzenediol 3-[2-[3-Hydroxyphenyl]ethyl]-4[2-[3-[2-[2-phenylethylamino]ethanesulphonyl]propanylamino]ethyl]-1,2-benzenediol 3-[2-[3-Hydroxyphenyl]ethyl]-4-[2-[6-[2-[4-nitrophenyl]ethylamino]hexylamino]ethyl]-1,2-benzenediol 4-[2-[6-[2-[4-Aminophenyl]ethylamino]hexylamino]ethyl]-3-[2-[3-hydroxyphenyl]ethyl]-1,2-benzenediol 4-[2-[6-[2-[3,4-Dihydroxy-2[2[3-hydroxyphenyl]ethyl]phenylethylamino]hexylamino]ethyl]-3-fluoro-1,2-benzenediol 4-[2-[6-[3-Fluoro-4-hydroxyphenyl]ethylamino]hexylamino]ethyl]-3-[2-[3-hydroxyphenyl]ethyl]-1,2-benzenediol 3-[2-[3-Methylphenyl]ethyl-4-[2-[6-[2-phenylethylamino]hexylamino]ethyl]-1,2-benzenediol 4-[2-[6-[2-[4-Hydroxyphenyl]ethylamino]hexylamino]ethyl]-3-[2-[3-methylphenyl]ethyl]-1,2-benzenediol 3-[2-[3-Hydroxyphenyl]ethyl]-4-[2-[8-[2-[4-hydroxyphenyl]ethylamino]octylamino]ethyl]-1,2-benzenediol 4[2-[6-[2-Phenylethylamino]hexylamino]ethyl]-3-[2-[3-trifluoromethyl]phenyl]ethyl]-1,2-benzenediol 3-[2-[3,5-Dihydroxyphenyl]ethyl]-4-[2-[6-[2-phenylethylamino]hexylamino]ethyl]-1,2-benzenediol 4-[2-[6-[2-[3,4-Dihydroxyphenyl]ethylamino]hexylamino]ethyl]-3-[2-[3-hydroxyphenyl]ethyl]-1,2- benzenediol 3-[3-[3-Hydroxyphenyl]propyl]-4-[2-[6-[2-phenylethylamino]hexylamino]ethyl]-1,2-benzenediol 3-[3-[3-Hydroxyphenyl]propyl]-4-[2-[6-[2-[4-hydroxyphenyl]ethylamino]hexylamino]ethyl]-1,2-benzenediol 4-[2-[6-[2-[2,3-Dihydroxyphenyl]ethylamino]hexylamino]ethyl]-3-[2-[3-hydroxyphenyl]ethyl]-1,2-benzenediol 3-[2-[3-Chlorophenyl]ethyl]-4-[2-[6-[2-phenylethylamino]hexylamino]ethyl]-1,2-benzenediol 3-[2-[3-Chlorophenyl]ethyl]-4-[2-[6-[2-[4-hydroxyphenyl]ethylamino]hexylamino]ethyl]-1,2-benzenediol 4-[2-[6-[2-Cyclohexylethylamino]hexylamino]ethyl]-3-[2-[3-hydroxyphenyl]ethyl]-1,2-benzenediol 3-[2-[3-Hydroxyphenyl]ethyl]-4-[2-[6-[2-[4-hydroxyphenyl]ethylamino]hexylamino]ethyl]-1,2-benzenediol 3-[4-[3-Hydroxyphenyl]butyl]-4-[2-[6-[2-phenylethylamino]hexylamino]ethyl]-1,2-benzenediol E-3-[2-[3-Hydroxyphenyl]ethyl]-4-[2-[6-[2-phenylethylamino]-3-hexenylamino]ethyl]-1,2-benzenediol N-[4-[2-[6-[2-[3,4-Dihydroxy-2-[2-[3-hydroxyphenyl]ethehtyl]phenyl]ethylamino]hexylamino]ethyl]phenyl]methanesulphonamide 4-[2-[6-(2-Phenylethoxy)hexylamino]ethyl-3-[2-[3-hydroxyphenyl]ethyl]-1,2-benzenediol or a pharmaceutically acceptable salt or solvate thereof.

9. A pharmaceutical composition comprising a compound according to claim 1 in admixture with a pharmaceutically acceptable adjuvant, diluent or carrier.

10. A method of treatment of renal failure which comprises administration of an effective amount of a compound according to claim 1 to a patient suffering from such a condition.

* * * * *